United States Patent
Rymer

(10) Patent No.: US 7,014,818 B2
(45) Date of Patent: Mar. 21, 2006

(54) ELECTRICAL DEVICE FOR EVAPORATING VOLATILE LIQUID

(75) Inventor: Shaun Rymer, East Yorkshire (GB)

(73) Assignee: Reckitt Benckiser (UK) Limited, Slough (GB)

( * ) Notice: Subject to any disclaimer, the term of this patent is extended or adjusted under 35 U.S.C. 154(b) by 500 days.

(21) Appl. No.: 10/277,651

(22) Filed: Oct. 22, 2002

(65) Prior Publication Data

US 2005/0053528 A1    Mar. 10, 2005

Related U.S. Application Data

(63) Continuation of application No. PCT/GB01/00953, filed on Mar. 6, 2001.

(30) Foreign Application Priority Data

Mar. 6, 2000    (GB) .................................... 0005222

(51) Int. Cl.
*A62B 7/08* (2006.01)

(52) U.S. Cl. ...................... 422/123; 392/392; 392/395; 422/4; 422/5; 422/120; 422/125

(58) Field of Classification Search ................ 422/120, 422/123, 125, 4, 5; 392/392, 387, 395
See application file for complete search history.

(56) References Cited

U.S. PATENT DOCUMENTS

| | | | |
|---|---|---|---|
| 1,944,821 A | 1/1934 | Blaise | |
| 4,032,028 A * | 6/1977 | Reiss et al. | ................. 215/217 |
| 4,621,768 A | 11/1986 | Lhoste et al. | |
| 5,038,394 A * | 8/1991 | Hasegawa et al. | .......... 392/395 |
| 5,222,186 A | 6/1993 | Schimanski et al. | |
| 5,647,053 A | 7/1997 | Schroeder et al. | |
| 6,097,881 A * | 8/2000 | DeWitt et al. | .............. 392/392 |
| 6,104,867 A | 8/2000 | Stathakis et al. | |
| D433,744 S | 11/2000 | Basagañas | |
| D437,636 S | 2/2001 | Basagañas | |
| 6,236,807 B1 | 5/2001 | Ruffolo et al. | |
| D444,220 S | 6/2001 | Basagañas | |
| 6,278,840 B1 * | 8/2001 | Basaganas Millan | ....... 392/390 |
| 6,285,830 B1 | 9/2001 | Basaganas Millan | |
| 6,466,739 B1 | 10/2002 | Ambrosi et al. | |

FOREIGN PATENT DOCUMENTS

EP    0 362 397 A1    4/1990

(Continued)

*Primary Examiner*—Krisanne Jastrzab
(74) *Attorney, Agent, or Firm*—Akin Gump Strauss Hauer & Feld, LLP

(57) ABSTRACT

A device 1 for evaporating volatile liquids comprises a casing 2 and a bottle 3 containing the volatile liquid. the device 1 contains within it a heater which is heated by connecting the device into a wall socket by means of an electric plug 4.

The device comprises container-receiving means 40 which interact with engagement means 8 formed on the neck of the bottle 3. Release of the bottle is effected by means of a button 7 which causes deformation of the container-receiving means 40 leading to release of the bottle 3. The button 7 is located on the same face of the device 1 as the electric plug 4. This means that the button is not accessible whilst the device is connected to a wall socket. This prevents appropriate removal of the bottle 3 from the casing 2 whilst the device 1 is connected to an electric current.

11 Claims, 3 Drawing Sheets

FOREIGN PATENT DOCUMENTS

| | | |
|---|---|---|
| EP | 0 420 144 A1 | 4/1991 |
| EP | 0 736 248 A1 | 10/1996 |
| ES | 2 137 111 | 1/1999 |
| GB | 2 194 442 A1 | 3/1988 |
| WO | WO 98/19526 A1 | 5/1998 |
| WO | WO 98/58692 A1 | 12/1998 |

* cited by examiner

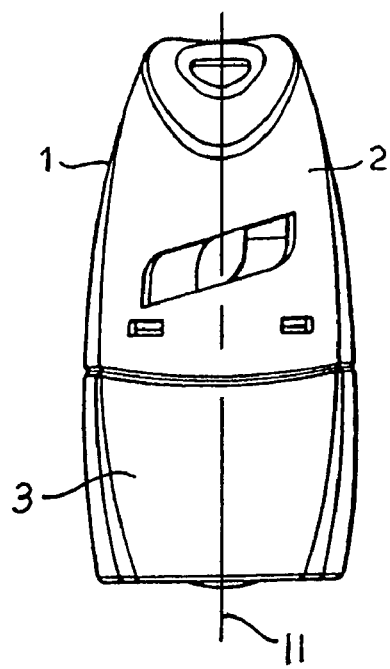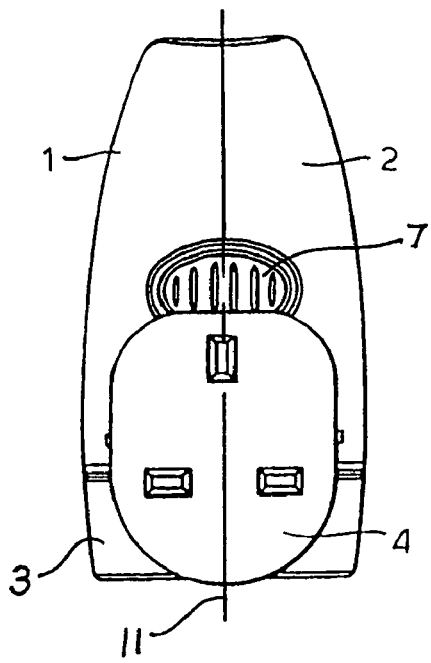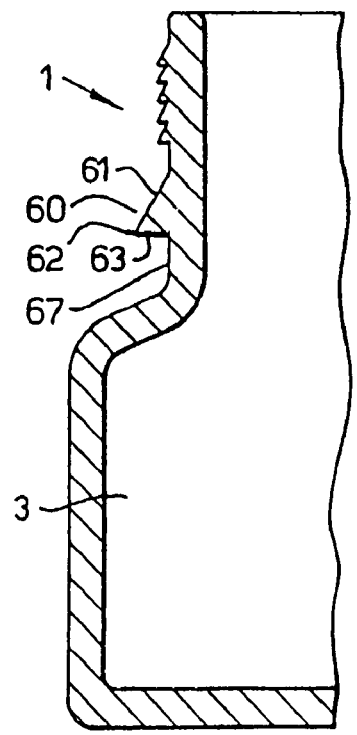

ELECTRICAL DEVICE FOR EVAPORATING VOLATILE LIQUID

CROSS-REFERENCE TO RELATED APPLICATIONS

This application is a continuation of International Application No. PCT/GB01/00953, filed Mar. 6, 2001, which was published in the English language on Sep. 13, 2001 as International Publication No. WO 01/66157 A1 and the disclosure of which is incorporated herein by reference.

BACKGROUND OF THE INVENTION

This invention relates to a device comprising a casing, and a container attachable to the container, and in particular to a device for evaporating volatile liquids, for example air fresheners and insecticides. The invention relates in particular to a device for evaporating volatile liquids from a container into a room, with the assistance of electrical power.

Devices are known, in which a bottle of volatile liquid has a wick projecting from it, and a heater is located in the vicinity of the distal end of the wick, to accelerate the evaporation of volatile liquid from the wick. The bottle, wick and heater are retained within a casing which carries an electrical plug. To operate the heater, the device is plugged into a wall socket.

Such devices are known, which purport to offer control of the rate of evaporation of the volatile liquids. In one device, described in Spanish Patent Application No. 9701388, the rate of evaporation is altered by varying the relative position of the wick and the heater (which typically is ring-shaped). In this patent application there is described a means for moving the container and the wick axially, through the action of a screw thread, whilst the ring heater is kept stationary.

In one device on the market, the relative movement of a ring heater and a wick is achieved by keeping the wick stationary and moving the heater axially.

In another device on the market, a tiltable barrel device is located at the distal end of the wick. This may be tilted about a horizontal axis to alter the airflow pathways at the distal end of the wick, and thereby alter the rate of evaporation.

In such devices, the bottle to which the wick is attached or connected, is removably connected to the casing. During use of the device, the volatile liquid within the bottle will in due course be consumed through evaporation and it will be necessary for a consumer to remove the empty bottle and replace it with a fresh bottle containing more volatile liquid. In order to remove the bottle from the casing, a consumer will first of all remove the device from a wall socket to which it is connected, and then release the bottle from the casing.

However, because the bottle must by definition be removable from the casing, there is a possibility that the bottle could be inappropriately removed from the casing whilst the device is connected to a source of electricity. For example, a young child having no understanding of the dangers of electricity could remove the bottle from the casing whilst the device is plugged into a wall socket. Removal of the bottle whilst the device is connected to a wall socket is potentially dangerous particularly for children who may for example attempt to insert one or more of their fingers into the heater. This could result in the child's finger becoming burnt, or under certain circumstances a child being subjected to an electric shock.

BRIEF SUMMARY OF THE INVENTION

According to a first aspect of the present invention there is provided a device comprising a container, and a casing attachable to the container, the container being removably connected to the casing, the casing comprising container-receiving means adapted to receive the container within the casing, and the container comprising engagement means adapted to engage with the container-receiving means such that the container is held securely within the casing, the device further comprising release means adapted to release the container from the casing by causing deformation of the container-receiving means.

According to a second aspect of the present invention there is provided a device for evaporating a volatile liquid, the device comprising: a container for the volatile liquid; a wick which has a proximal end region within the container, with the proximal end thereof adjacent to the base of the container and a distal end region above the container; an electric heater able to provide heat to the distal end region of the wick; a casing which extends over the container and wick, and which has an aperture above the distal end of the wick; characterized in that the casing comprises container-receiving means adapted to receive the container within the casing, and in that the container comprises engagement means adapted to engage with the container-receiving means in the casing such that the container is held securely within the casing during use, and further in that the device comprises release means adapted to release the engagement portion of the container from the container-receiving means of the casing to allow release of the container from the casing.

Thus, during use, a portion of the container is held in gripping contact with the container-receiving means.

Advantageously, the release means and the container-receiving means are integrally formed.

Preferably, the release means is in the form of a button, and the container-receiving means is formed from a resilient plastics material.

When the button is depressed, the container-receiving means outwardly deforms such that contact between the container and the container-receiving means is lost, thus allowing a container to be removed from or inserted into the casing as appropriate. When the button is released, the container-receiving means returns to its non-deformed position in which contact with the container is re-established thus preventing the container from being removed from the casing.

Advantageously, the container-receiving means comprises at least one, and preferably two clips each of which has a component extending substantially at right angles to the axis of the device, and the engagement portion of the container comprises a ridge extending at least partially around a portion of the container, preferably a neck of the container.

Preferably the extending component of each clip has beveled edges viewed either in plan or side view or both.

The ridge preferably extends around the entire circumference of the neck of the container. Alternatively, however, it could extend around only part of the circumference of the neck, or it could comprise a plurality of ridge portions positioned around the circumference of the neck.

In use, the one or more clips make contact with the container below the ridge of the container. When the container-receiving means is in a non-deformed state, in other words when the button has not been depressed, the one or more clips will make contact with the container, and the presence of the ridge will prevent the bottle from being pulled out of the casing.

Preferably, the container-receiving means comprises two clips spaced apart from one another and positioned such that in use each of the clips is adapted to grip an opposite side of the container. The clips are thus positioned substantially diametrically opposite one another.

Each clip has a container-gripping edge each of which edges in use makes contact with a surface of the container. Preferably the container-gripping edges are shaped to be complementary to the shape of the container. The edges may for example be arcuately shaped to accommodate an annular shaped container.

In use the distance between the respective edges of the clips is less than the outer diameter of the ridge. This means that in use, the presence of the ridge will prevent the bottle from being removed from the casing.

When it is required to remove the container from the casing, the effect of depressing the button is to cause deformation of the container-receiving means which deformation causes the clips to move away from the container and out of contact with the container. The degree of deformation is such that the distance between the edges of the clips becomes substantially greater than the outer diameter of the ridge. This means that the container is now free to pass through the container-receiving portion of the casing, and be removed from the casing.

Advantageously, in cross-section the ridge comprises a sloping upper surface, and a lower surface lying substantially in a plane at right angles to the axis of the device.

In use, when it is required to insert a bottle into the casing, it is not always necessary to depress the button. Instead, as the bottle is inserted into the casing, the ridge will come into contact with the two clips. Because the upper surface of the ridge is sloping, as the bottle is inserted into the casing, the clips will be pushed towards the bottom edge of the upper surface of the ridge. Due to the slope of the upper surface of the ridge, this movement will cause the clips to move outwardly until the clips are in contact with the lower edge of the upper surface of the ridge. At this point, further movement of the bottle towards the casing will cause the clips to move past the upper surface of the ridge. Due to the inherent memory of the plastics material, the clips will snap back into their original position engaging the bottle beneath the ridge.

Advantageously, the casing further comprises a plug suitable for insertion into an electric wall socket in order to supply electricity to the device. In such devices the release means is positioned such that it is inaccessible to a user when the device is plugged into an electric socket. For example, the release means is positioned on the same face of the container as the electric plug. This means that once the device is connected to the wall socket, the wall will prevent access to the release means.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIG. 1 is a front view of a device for evaporating volatile liquids according to a first embodiment of the present invention;

FIG. 2 is a rear view of the device of FIG. 1;

FIG. 6a is a detailed representation of part of the bottle 6 showing the shape of the engagement portion of the bottle of FIG. 6.

DETAILED DESCRIPTION OF THE INVENTION

Figure 3:
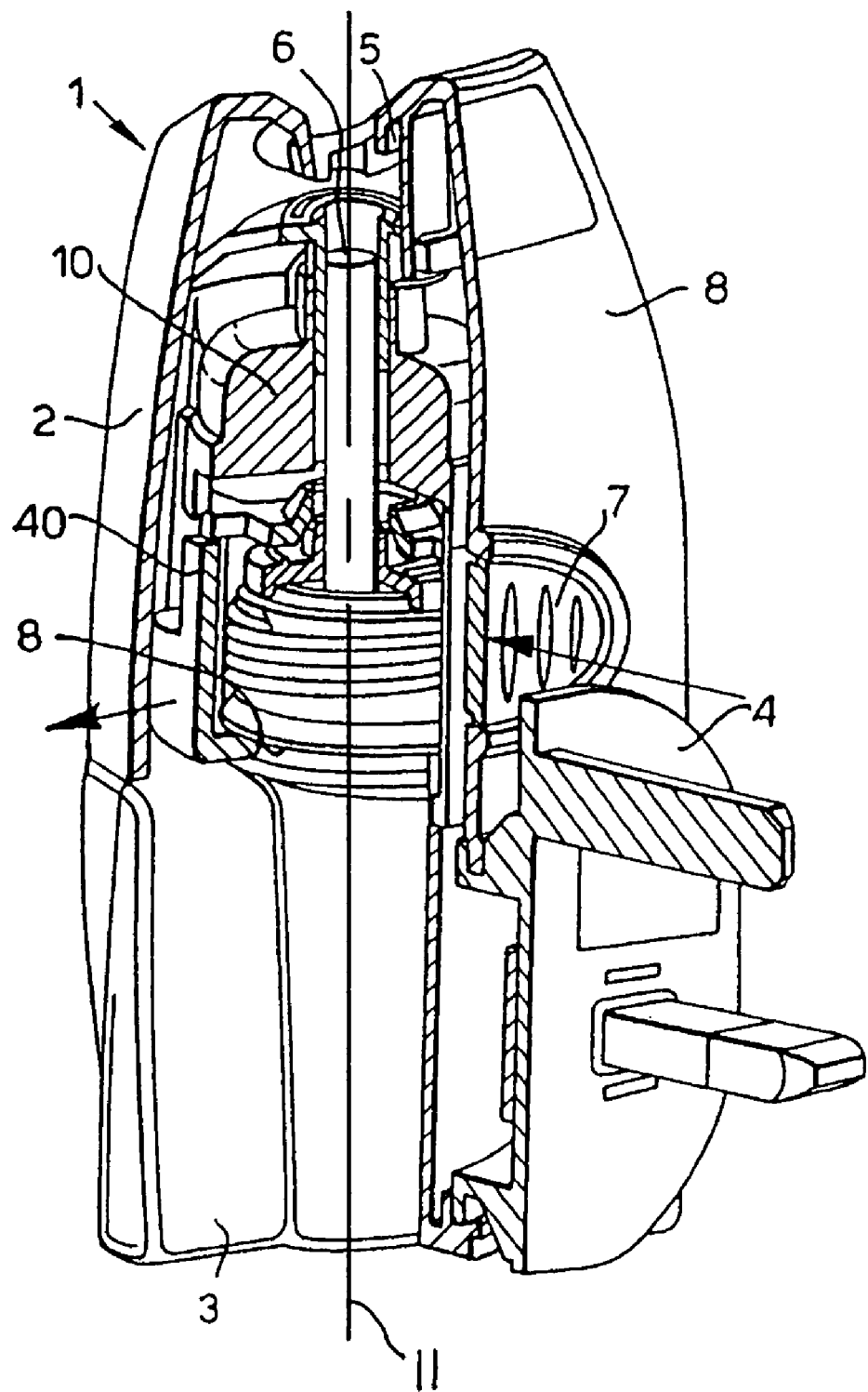
FIG. 3 is a partially cut away view of the device of FIGS. 1 and 2 showing the container-receiving means of the device according to a first embodiment of the present invention.
Figure 4:
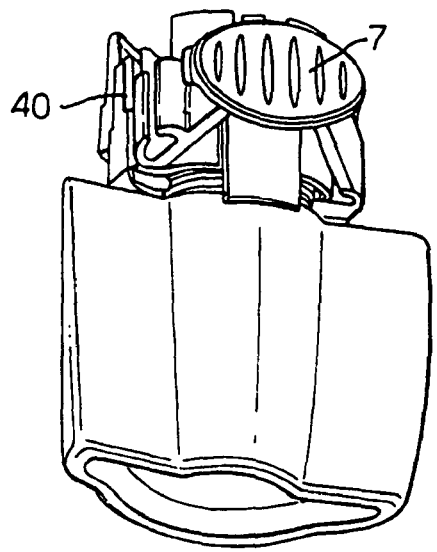
FIG. 4 is a schematic representation of the container and container-receiving means of the device of FIG. 3 showing the container-receiving means in its non-deformed state.
Figure 5:
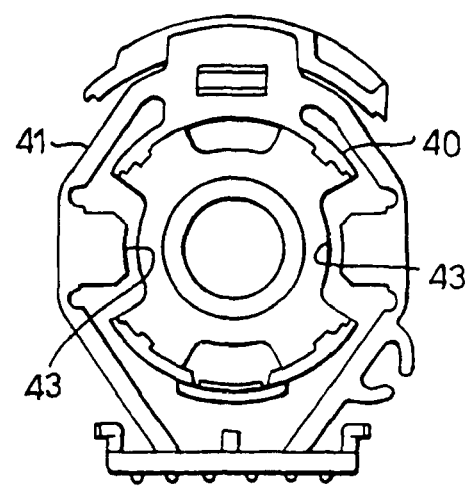
FIG. 5 is a cross-sectional representation of the container-receiving means in its non-deformed state.

Referring to the Figures, the device according to the present invention is designated generally by the reference numeral 1 for evaporating volatile liquids for example air fresheners and insecticides. The device 1 further comprises a casing 2 to which is attached a container 3 which in this example is in the form of a bottle. The device 1 contains within it a heater 10 which is operated by connecting the device 1 to a source of electricity by means of an electric plug 4 which is connectable to an electric wall socket (not shown). The bottle 3 contains within it a volatile liquid impregnated with for example a fragrance. The bottle has projecting from it a wick 5, and the heater 10 is located in the vicinity of the distal end 6 of the wick 5. The heater accelerates the evaporation of volatile liquid from the bottle 3. The bottle 3 together with the wick 5, which is connected to the bottle 3, are retained within the casing 2 by means of a container-receiving means 40 located within the casing 2. The container-receiving means 40 comprises a collar 41 formed from a deformable plastics material. The collar 41 further comprises clips 42 spaced apart from one another and lying in a plane substantially at right angles to the axis 11 of the device 1. The clips 42 are positioned substantially diametrically opposed to one another and comprise bottle-gripping edges 43. The device 1 further comprises release means 7 in the form of a button accessible via a face 8 of the device 1.

The bottle 3 comprises engagement means 8 which in this embodiment are in the form of a ridge running circumferentially around the neck 9 of the bottle 3. The ridge 8 extends around the circumference of the neck 9. The outer edge 60 of the ridge 8 defines a ring having a diameter which clearly is greater than the diameter of the neck 9 of the bottle 3.

When the container-receiving means 40 is a non-deformed state, the distance between of edges 43 of the clips 42 is substantially the same as the diameter of the neck 9 of the bottle 3, and substantially less than the outer diameter of the ridge 60. This means that in use, the bottle 3 will be held in position within the casing 2 by the clips 42 which will make contact with the neck 9 of the bottle 3.

Figure 7:
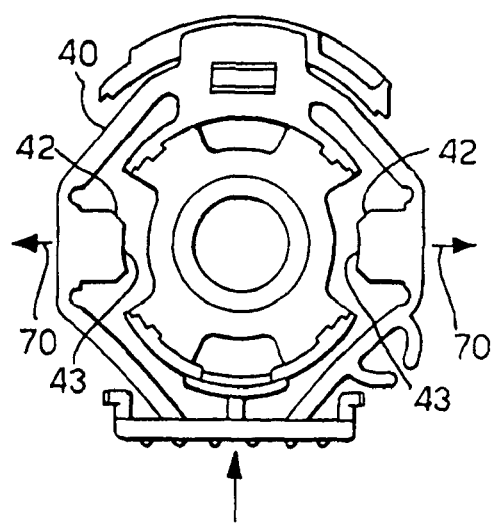
FIG. 7 is a cross-sectional representation of the container-receiving means in its deformed state.

When it is required to release the bottle from the casing, a user must depress button 7. Because button 7 is formed integrally with the container-receiving means 40, depression of button 70 causes deformation of the collar 41 causing the clips 42 to move away from one another in the direction of the arrows 70 in FIG. 7. The extent of deformation of the collar 41 is such that the distance between the edges 43 now increases to be substantially greater than the outer diameter of the ridge 60. This allows the bottle neck to pass through the collar 41 unimpeded. In use this means that the user will be able to remove the bottle from or introduce the bottle into the casing of device 1, as appropriate, by depressing button 7.

Because the button 7 is located on the same face as the electric plug 4, when the device is connected to an electrical wall socket, the button 7 will be inaccessible since it will be in contact with or very close to the wall in which the wall socket is located. It would thus be impossible to depress the button in order to cause deformation of the collar 41 to allow release of the bottle.

This means that it should be very difficult, if not impossible for somebody such as for example a young child to pull the bottle 3 away from the casing 2 whilst the device is connected to a source of electricity.

Figure 6:
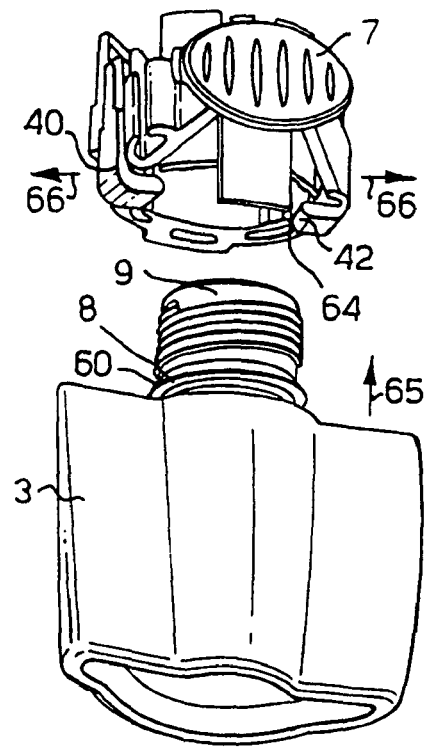
FIG. 6 is a schematic representation showing the container-receiving means in a deformed state allowing release of the container from the container-receiving means.

As can be seen particularly from FIG. 6a, the ridge 60 is substantially triangular in cross-section, having an upper slope 61 which slopes outwardly towards the bottom of the bottle 3 to a point 62 at which the diameter of the ridge is at a maximum. The ridge further comprises an undersurface 63 which is substantially flat lying substantially in a plane at right angles to the axis 11 of the device 1.

The clips 42 each comprise an underneath surface 64 (as shown particularly in FIG. 6) which slopes in a similar manner to the upper surface 61 of the ridge 60. In use, when it is required to insert a bottle 3 into the casing 2, it is not necessary to depress the button 7. Instead, due to the sloping upper surface 61 of the ridge 60, and the sloping undersurface 64 of the clips 42, and further due to the deformable characteristics of the collar 41, when the bottle 3 is inserted into the casing 2 the underneath surfaces 64 of the clips 42 will engage with the upper surface 61 of the ridge 60, and movement of the bottle in the direction shown generally by arrow 65 will cause the clips to move outwardly in the direction of arrows 66. When the clips 42 move beyond a lower point 62 of the ridge 60, there will no longer be a surface of the ridge holding the clips in a deformed position. Due to the inherent memory of the plastics material, the clips will snap back into an undeformed position in which they make contact with the surface 67 of the bottle 3 and the underneath surface 63 of the ridge 60. In this position the bottle will be held securely in place.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A device comprising:
    a container having an engagement portion;
    a casing;
    a receiver within the casing, the receiver adapted to releasable engage the engagement portion and securely hold the container within the casing; and
    a release adapted to release the container from the casing by causing deformation of the receiver, the release being moved radially inwardly relative to an axis of the device resulting in at least a portion of the receiver deforming radially outwardly relative to the axis to release the container from the casing.

2. A device for evaporating a volatile liquid, the device comprising:
    a container for the volatile liquid, the container having a base and an engagement portion;
    a wick having a proximal end region and a distal end region, the proximal end region within the container, a proximal end of the proximal end region adjacent to the base of the container, the distal end region above the container;
    an electric heater able to provide heat to the distal end region of the wick;
    a casing extending over the container and the wick, the casing having an aperture above the distal end of the distal end region of the wick;
    a receiver within the casing, the receiver adapted to releasable engage the engagement portion and securely hold the container within the casing; and
    a release adapted to release the engagement portion of the container from the receiver to allow release of the container from the casing, the release being moved radially inwardly relative to an axis of the device resulting in at least a portion of the receiver deforming radially outwardly relative to the axis to release the container from the casing.

3. The device according to claim 1, wherein the release and the receiver are integrally formed.

4. The device according to claim 1, wherein the release is in the form of a button, and the receiver is formed from a resilient plastics material.

5. The device according to claim 1, wherein the receiver comprises at least one clip having a component extending substantially at right angles to the axis, and the engagement portion of the container comprises a ridge extending at least partially around a portion of the container.

6. The device according to claim 5, wherein the container has a neck and the ridge extends at least partially around the neck.

7. The device according to claim 5, wherein the receiver comprises two clips spaced apart from one another and positioned such that in use each of the clips is adapted to grip an opposite side of the container.

8. The device according to claim 5, wherein the clip comprises a container-gripping edge.

9. The device according to claim 5, wherein, in cross-section the ridge comprises a sloping upper surface, and a lower surface lying substantially in a plane at right angles to the axis.

10. The device according to claim 1, wherein the casing further comprises a plug suitable for insertion into an electric wall socket in order to supply electricity to the device.

11. The device according to claim 10, wherein the casing has a face and the plug and release are located on the face.

* * * * *